United States Patent [19]

Garner

[11] Patent Number: 5,241,363
[45] Date of Patent: Aug. 31, 1993

[54] MICROPIPETTE ADAPTOR WITH TEMPERATURE CONTROL FOR PCR AMPLIFICATION

[75] Inventor: Harold R. Garner, Encinitas, Calif.
[73] Assignee: General Atomics, San Diego, Calif.
[21] Appl. No.: 843,443
[22] Filed: Feb. 28, 1992

Related U.S. Application Data

[63] Continuation-in-part of Ser. No. 407,539, Sep. 15, 1989, Pat. No. 5,092,674, which is a continuation-in-part of Ser. No. 377,476, Jul. 10, 1989, Pat. No. 4,991,958.

[51] Int. Cl.$^5$ .................... G01N 21/01; G01N 21/31
[52] U.S. Cl. .................... 356/326; 356/244; 356/436
[58] Field of Search ............ 356/244, 326, 328, 432, 356/436

[56] References Cited

U.S. PATENT DOCUMENTS

| | | | |
|---|---|---|---|
| 3,877,817 | 4/1975 | Ralston | 356/180 |
| 4,006,990 | 2/1977 | Munk | 356/246 |
| 4,440,497 | 4/1984 | Carey et al. | 356/246 |
| 4,935,875 | 6/1990 | Shah et al. | 364/497 |
| 4,991,958 | 2/1991 | Garner | 356/244 |
| 5,092,674 | 3/1992 | Garner | 356/244 |

Primary Examiner—Vincent P. McGraw
Attorney, Agent, or Firm—Nydegger & Associates

[57] ABSTRACT

A temperature-controlled micropipette adaptor includes a metal base sandwiched between two plastic layers. The metal base has an orifice to hold a micropipette. The plastic layers hold lenses in alignment for spectrophotometric measurements of a sample contained in a micropipette inserted into the orifice. A resistive heater wire or thermoelectric heater/cooler is held between the metal base and the plastic layer to transfer heat from the heater wire or thermoelectric device to the metal base and thus to the micropipette sample. A thermocouple is attached to the metal layer to monitor temperature changes. A feedback control system is coupled to the device for monitoring and programmably controlling changes in temperature of the heated sample over time. As desired, a microprocessor can be electrically connected between the heater wire or thermoelectric device and the output signal of the spectrophotometer to selectively energize the heater wire thermoelectric device in response to the output signal of the spectrophotometer.

14 Claims, 4 Drawing Sheets

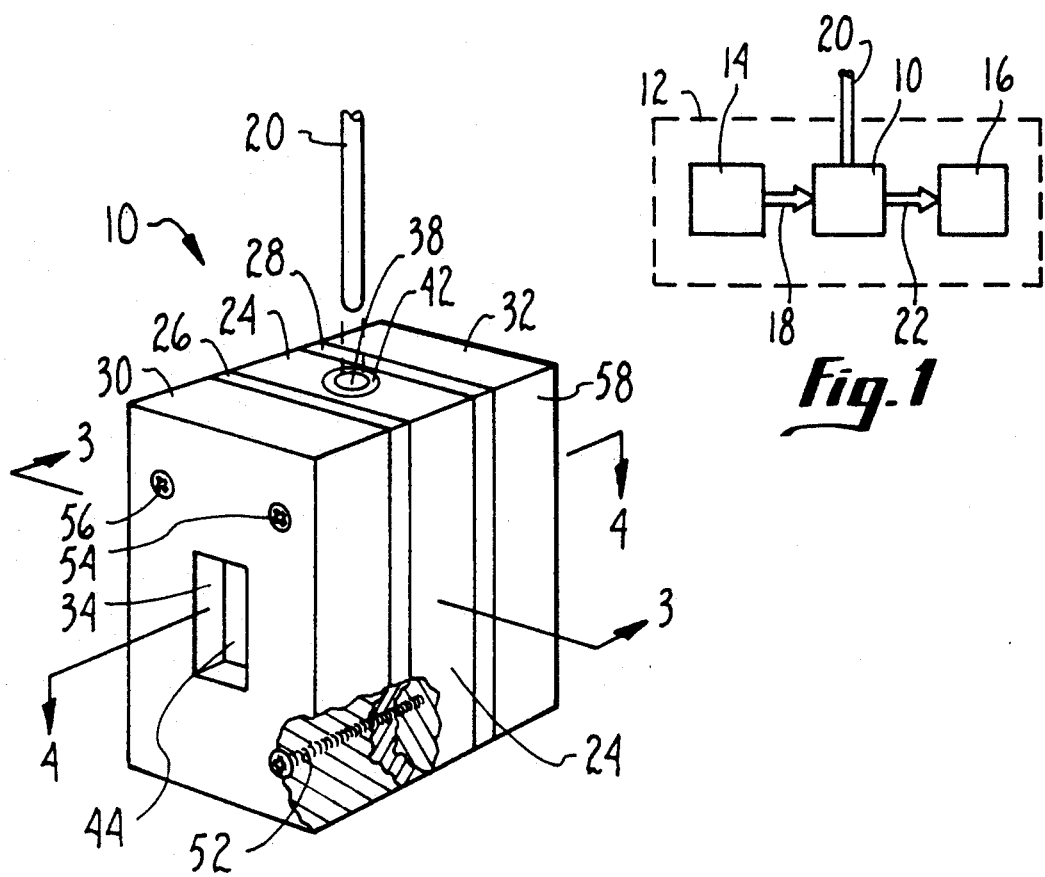
Fig. 1
Fig. 2
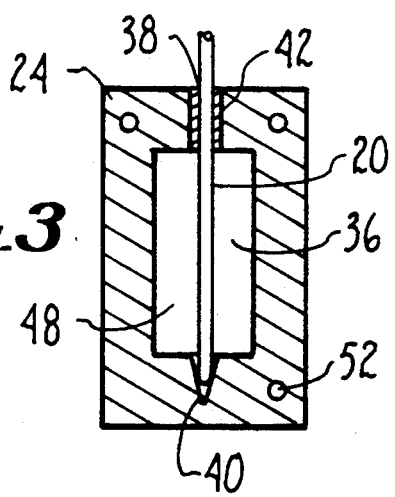
Fig. 3
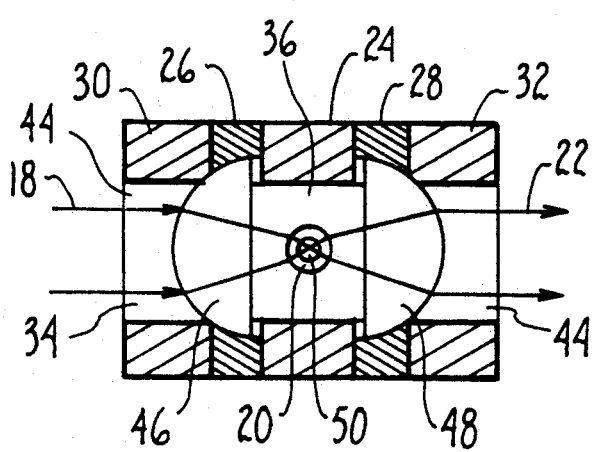
Fig. 4

MICROPIPETTE ADAPTOR WITH TEMPERATURE CONTROL FOR PCR AMPLIFICATION

FIELD OF THE INVENTION

This application is a continuation-in-part of our prior application Ser. No. 407,539 filed Sept. 15, 1989, now U.S. Pat. No. 5,092,674, which is a continuation-in-part of Ser. No. 377,476 filed Jul. 10, 1989, now U.S. Pat. No. 4,991,958.

The present invention pertains to devices which hold sample materials while the composition of the material is being measured and analyzed. Specifically, the present invention pertains to sample holders which may be used with spectrophotometers, and colorimeters. The present invention is particularly, but not exclusively, useful for obtaining spectroscopic measurements of very small samples of material while being heated.

BACKGROUND OF THE INVENTION

The use of spectrophotometers to measure the light absorption characteristics of sample materials is well known. Indeed, the basic principles involved are relatively simple. A beam of light, whose characteristics are known, is directed through the sample material and the light that emerges is analyzed to determine which wavelengths of the original beam were absorbed, or otherwise affected, by the sample material. Based on differences between the incident light and the transmitted light, certain characteristics of the sample material can be determined. Many variables are involved, however, that can make a spectrophotometric measurement quite complex. In sum, these complexities arise from the fact that the sensitivity and accuracy of a measurement rely on the ability of the spectrophotometer to measure the light which is absorbed by the samples.

Analytically, a spectrophotometric analysis relies on a known relationship of the variables involved. Specifically, in a standard spectrophotometric measurement, the amount of light transmitted through a test cuvette is measured and the percent of transmitted light is related to the material in the cuvette by the following relationship:

$$I_t(\lambda) = I(\lambda) 10^{-OD}$$

where $I(\lambda)$ and $I_t(\lambda)$ are respectively the input and transmitted intensities, and the optical density, OD, is given by:

$$OD = a(\lambda) L C$$

where $a(\lambda)$ is the absorptivity of the material as a function of $\lambda$, L is the optical path length, and C is the concentration. From the above, it will be easily appreciated that the output intensity $I_t(\lambda)$ is directly proportional to the input intensity $I(\lambda)$. Therefore, it is clearly necessary to have an input intensity that is sufficient to give an output intensity which can be effectively used for analysis and measurement of the sample material. Further, the efficacy of the measurement will also be enhanced if the concentration of the sample material is increased. Thus, for spectrophotometric analysis it is desirable to have a light input of high intensity, and have a highly concentrated sample in solution. There is a problem, however, when low concentration solutions of sample material are available in only very small quantities (e.g. 0.5 to 50 micrograms/microliter).

To be effective for spectroscopic measurements, test cuvettes for holding the sample material must be completely filled. This typically requires a substantial amount of sample material. Consequently, when only a small amount of the sample material is effectively available for testing, presently available test cuvettes (e.g. 12.5 mm × 12.5 mm cuvette) are inadequate because of their relatively large size. Merely reducing the size of the cuvette is not the answer. This is so because, with a size reduction of the cuvette there is also a reduction in the amount of sample material through which light can pass. Consequently, the intensity of the light passing through the sample material is reduced and the sensitivity and accuracy of the measurement is compromised.

The present invention recognizes that it is possible to take spectrophotometric measurements of very small quantities of a sample material, even where there is a relatively low concentration of the material in solution. The present invention recognizes that this can be done by properly focusing collimated light onto the sample material to obtain sufficiently high input light intensities for the desired measurements. Further, the present invention recognizes that this focusing can be accomplished by a device which is engageable, and operatively compatible, with presently available spectrophotometers such as a UVIKON Model 820 spectrophotometer by Kontron.

The present invention further recognizes that occasionally it is important to make spectroscopic observations of small samples at various controlled elevated temperatures. For example, for DNA material, it is known that the double strands of DNA break into two single strands (denatures) at temperatures above 70° C. This denaturing of the DNA is also known to result in a significant increase in the light absorption of the sample. It is desirable to spectroscopically monitor denaturization. It is also desirable to spectroscopically monitor enzymatic and other thermally-induced reactions in small biological, as well as nonbiological, samples. For example, the progress of a process known as polymerase chain reaction (PCR), disclosed in U.S. Pat. No. 4,683,202, can be studied using spectroscopic techniques. The PCR process involves repeatedly denaturing and assembling DNA in the presence of oligonucleotide primers to amplify the DNA. In this context, assembly consists of two parts, binding of the primers to the target DNA and extension from the primer sites by the polymerization of nucleotides to form double stranded DNA. More particularly, the PCR process requires cyclically heating the DNA sample in accordance with a predetermined temperature profile schedule to raise the temperature above the denaturing temperature for a predetermined dwell time and the reducing the temperature to below the denaturing temperature for a predetermined dwell time to allow the single strands to assemble from primers and nucleotides (C,G,A,T) into double strands. Unfortunately, the precise denaturation and assembly temperatures and dwell times of the PCR technique can be difficult to optimize. Optimum temperatures and dwell times are desirable in order to achieve relatively fast and efficient DNA amplification.

Importantly, as the DNA solution undergoes the cyclic denaturation/assembly of the PCR process, the light absorption characteristics of the solution change. Consequently, by observing the light absorption characteristics of the DNA solution over time, the actual progress of the PCR process can be monitored. Stated differently, the changes in the light absorption characteristics of the DNA solution can be correlated to changes in the constituent composition of the DNA solution. Consequently, the present invention recognizes that the predetermined temperature profile schedule can be changed in response to the observed changes in the light absorption characteristics of the DNA solution, in order to optimize the PCR process.

In particular, the present invention recognizes that the absorption of light at 260 nm, as observed by a spectrophotometer, reveals the amount of target/product DNA, nucleotides and oligonucleotide primer present in the DNA solution because each constituent exhibits a different absorption strength. Since there is a difference between light absorption of single stranded DNA and double stranded DNA, i.e., single stranded DNA exhibits greater absorption, the total amount of target/product DNA can be determined from the difference between absorption at the denaturation and assembly temperatures.

Additionally, light absorption can be used to monitor the quantities of other materials such as enzymes (polymeration agents), in the DNA solution which are essential to the PCR process. For example, the enzyme thermus aquatics (TAQ) is known to absorb light at 280 nm. Therefore, the amount of intact, i.e. undamaged, TAQ present in the DNA solution is determined by monitoring light absorption at 280 nm.

The present invention further recognizes that it is possible to monitor spectrophotometric and spectrofluorometric changes at biologically significant temperatures. Study of bacteria or virus growth at human body temperatures of 37° C. could also be possible. In addition, nonbiological chemical reactions at temperatures elevated above room temperature can also be studied. The present invention accomplishes this by providing an apparatus which allows heating of the very small quantities of sample material in a controlled and efficient manner.

In light of the above, it is an object of the present invention to provide a micropipette adaptor for spectrophotometers which allows for spectrophotometric measurements of very small quantities of sample material in solution. Another object of the present invention is to provide a micropipette adaptor for spectrophotometers which permits recovery of the sample material after spectrophotometric measurements have been made. Yet another object of the present invention is to provide a micropipette adaptor for spectrophotometers which allows spectroscopic measurements of samples while the sample is in the process of being transferred through a micropipette. Still another object of the present invention is to provide a micropipette adaptor for spectrophotometers which provides for a high light collection efficiency to increase the sensitivity of the measurements which are made. Another object of the present invention is to provide a micropipette adaptor for spectrophotometers which allows a micropipette or other capillary sample holder to be easily installed and removed from the adaptor. Yet another object of the present invention is to provide a micropipette adaptor for spectrophotometers which provides approximately the same intensity light path length product for small samples as is provided for larger samples. Another object of the present invention is to provide a micropipette adaptor for spectrophotometers which is relatively easy to manufacture and comparatively cost-effective to operate.

Further, an object of the present invention is to provide a micropipette adaptor in which the temperature of the sample may be controlled. Another object of the present invention is to provide such a temperature-controlled micropipette adaptor which may be used in commercially available spectrophotometers. Yet another object of the present invention is to provide a temperature-controlled micropipette adaptor capable of easily attaining higher sample temperatures, and capable of maintaining predetermined temperatures for desired lengths of time. Another object of the present invention is to provide a temperature-controlled micropipette adaptor which is relatively simple and convenient to manufacture and use.

SUMMARY OF THE INVENTION

The micropipette adaptor for spectrophotometers according to the present invention comprises a base member which is adapted to hold a capillary tube, such as a micropipette, which is filled with a solution of the sample material to be analyzed. More specifically, the base member is formed with an opening, and is formed with a hole which is distanced across the opening from a conical well. As formed on the base member, both the hole and the conical well are aligned with each other to respectively receive a portion of the micropipette and hold it on the base member. When so held, the micropipette extends across the opening of the base member to permit light to pass through the micropipette.

An optical system is provided for the adaptor and is attached to the base member to both focus a beam of collimated light onto the micropipette, and to recollimate the light that has passed through the micropipette. For focusing the beam of collimated light, a cylindrical quartz lens (i.e. a directing lens) is positioned between the base member and the source of collimated visual or ultraviolet light. Specifically, this directing lens is used to focus collimated light from the light source into a line. In accordance with present invention, this linearly focused light is aligned along the longitudinal axis of the micropipette to provide a very high intensity light input for the sample material which fills the lumen of the micropipette. Another cylindrical quartz lens (i.e. a receiving lens) is positioned behind the base member to receive the light which has passed through the sample material in the pipette and to recollimate it for analysis and measurement by a detector.

As contemplated by the present invention, both the directing lens and the receiving lens are respectively held by holders which are positioned on opposite sides of the base member. Importantly, each of these holders is independently adjustable in its position relative to the base member. Thus, the directing lens may be independently moved relative to the micropipette to achieve alignment of its linearly focused light with the axis of the micropipette. Similarly, the receiving lens may be moved relative to the micropipette to achieve effective recollimation of the light that has passed through the micropipette. This recollimated light is then received by a detector in the spectrophotometer for further spectroanalysis. It will be appreciated by the skilled artisan that, depending on the wavelength of the light, the receiving lens and the directing lens may be made of quartz, glass, sapphire, fused silicon or any other appropriate light transmitting material.

The temperature control feature of the micropipette adaptor includes a metal base member sandwiched between two plastic material layers. The metal base member has an orifice adapted to hold a micropipette containing a sample material solution for analysis. The plastic material layers each have a lens mounted on either side of a passageway in the center of the base member, which forms the optical system to focus the collimated light through the sample in the micropipette. A resistive heater wire is held between the metal base and one of plastic layers, in position against the surface of the metal base, to transfer heat from the heater wire to the metal base. Similarly a thermoelectric heater/cooler could be used in place of or with the heater wire. The metal base includes a thermocouple which provides a signal representative of the temperature of the metal base, which allows the temperature of the sample material to be monitored. The micropipette of sample material is inserted into the orifice of the metal base and heated to a desired temperature. The metal base acts as a thermal reservoir for heating the sample, in addition to maintaining the alignment between the micropipette sample and the focusing lens. By choosing a base material of high thermal conductivity, such as copper, brass, or aluminum, the temperature of the sample in the micropipette can be increased quickly and maintained at a desired level.

The micropipette adaptor further includes a temperature feedback control system to maintain the sample at any desired temperature. The control system comprises an analog thermocouple gauge display driver, a digital panel meter, a comparator, a set point programmer, and a transistor heater driver. Also provided is an external input to allow programming of desired temperature variations over time.

As contemplated by the present invention, the adaptor is intended for use with very small micropipettes. For example, it is within the contemplation of the present invention that a micropipette having a capillary tube with a lumen which is approximately half a millimeter (0.5 mm) in diameter can be effectively used with the adaptor disclosed herein. Even so, it will be appreciated by the skilled artisan that pipettes of various sizes may be used. Furthermore, it is to be appreciated that the light wavelengths which are useful with the adaptor of the present invention need not necessarily be limited to the visual and ultraviolet ranges.

In another embodiment, apparatus for monitoring and controlling the heating of a solution that is held in a transparent container, e.g., a micropipette includes the heated metal base disclosed above. The base is formed with a cavity for receiving the micropipette. The base is positionable within a spectrometer to establish a light pathway from the light source of the spectrometer, through the cavity, container, and solution, and to the light receiver of the spectrometer. To heat the solution, the base includes a heating wire which circumscribes the cavity and can also include the temperature control feedback system described above.

A voltage source is electrically connected to the heating wire to energize the wire, and a microprocessor is electrically connected to the voltage source to control the voltage source. Accordingly, the microprocessor can selectively energize the voltage source to in turn cause the heating wire to be selectively energized in order to establish a predetermined time-dependent temperature profile of the solution held within the micropipette.

Importantly, the light interaction characteristics of the solution can change over time as the solution is alternatingly warmed and cooled. These light absorption characteristic changes are detected by the light receiver of the spectrometer. The microprocessor is electrically connected to the light receiver and the time dependent temperature profile of the solution, as indicated by the signal from the light receiver, is consequently monitored by the microprocessor. In accordance with the present invention, the microprocessor can alter the predetermined time dependent temperature profile of the solution in response to the spectrophotometer output signal to optimize the cyclic heating process of the solution.

The novel of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a schematic diagram showing the micropipette adaptor in its operative relationship with elements of a spectrophotometer;

FIG. 2 is a perspective view of the micropipette adaptor with selected elements shown in phantom and portions broken away for clarity;

FIG. 3 is a cross-sectional view of the micropipette adaptor as seen along the line 3—3 in FIG. 2;

FIG. 4 is a cross-sectional view of the micropipette adaptor as seen along the line 4—4 in FIG. 2;

DESCRIPTION OF THE PREFERRED EMBODIMENT

Figure 5:
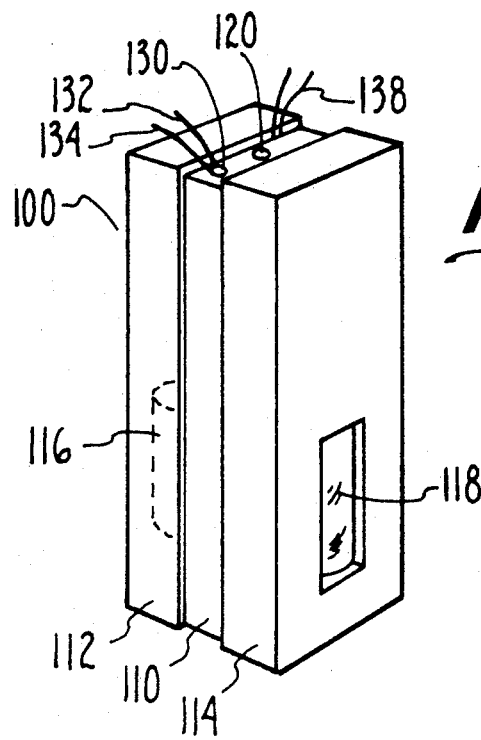
FIG. 5 is a perspective view of a micropipette adaptor having temperature control in accordance with the present invention.
Figure 6:
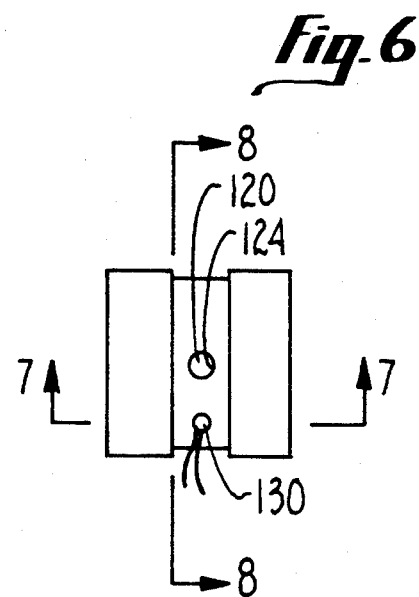
FIG. 6 is a top view of the adaptor with temperature control of FIG. 5.
Figure 7:
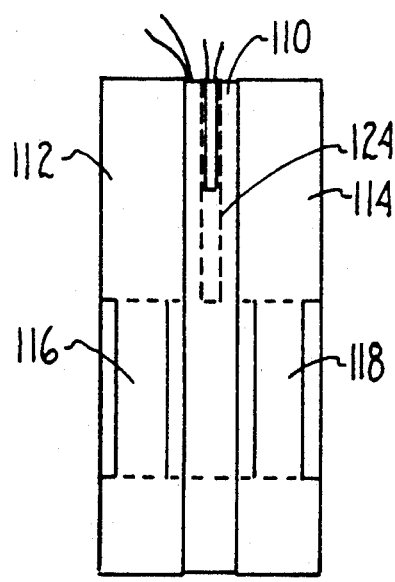
FIG. 7 is a cross-sectional view of the adaptor with temperature control as seen along line 7—7 of FIG. 6.
Figure 8:
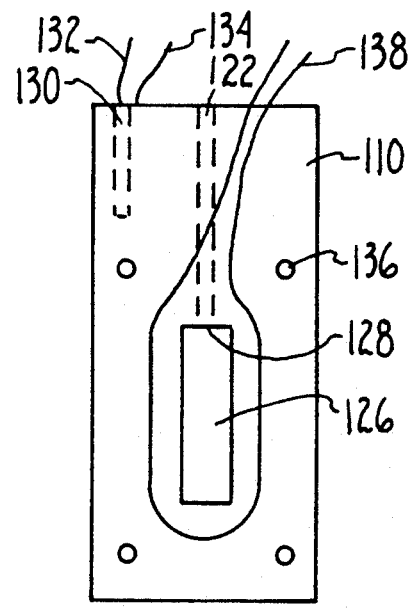
FIG. 8 is a cross-sectional view of the adaptor with temperature control as seen along the line 8—8 of FIG. 6.

Referring initially to FIG. 1, the micropipette adaptor for spectrophotometers in accordance with the present invention is schematically shown in its operative environment and is designated 10. As shown, adaptor 10 is positioned for operative engagement with a spectrophotometer 12 and, specifically, is positioned between a light source 14 and a detector 16. As so positioned, an input beam of collimated light 18, having an intensity $I(\lambda)$, is directed from the light source 14 toward the adaptor 10. In a manner to be subsequently disclosed, adaptor 10 focuses the beam 18 of collimated light onto a micropipette 20 which is held by the adaptor 10.

Adaptor 10 then recollimates this light into an output light beam 22 which has an intensity of $I_f(\lambda)$. As will be appreciated by the skilled artisan, the difference between $I(\lambda)$ and $I_f(\lambda)$ is indicative of the light absorption characteristics of the sample material held in micropipette 22 and, hence, is an indication of the composition of the sample material.

The construction of adaptor 10 will, perhaps, be best seen by reference to FIG. 2 wherein it is shown that adaptor 10 comprises a base member 24 which is sandwiched between a resilient member 26 and a resilient member 28. Respectively positioned against resilient members 26 and 28 and opposite base member 24 are holders 30 and 32. Preferably, base member 24 and the holders 30 and 32 are made of a rigid material, such as black delrin plastic, while the resilient members 26 and 28 are made of an elastomeric material such as rubber or foam plastic. For purposes of the present invention, holder 30 is formed with an opening 34 as shown in FIG. 2, and base member 24, resilient members 26, 28 and holder 32 are each formed with openings (not shown in FIG. 2) which are aligned with opening 34 to establish a pathway 44 which allows light to pass through adaptor 10.

Referring now to FIG. 3, it will be seen that base member 24 is formed with an opening 36 which, as indicated above, is positioned in alignment with opening 34 of holder 30. Further, base member 24 is shown formed with a hole 38 and a conical-shaped well 40 which are positioned across the opening 36 from each other. Specifically, hole 38 and conical well 40 respectively receive portion of micropipette 20 to hold the micropipette 20 in place within and across the opening 36. A bushing 42, which is appropriately sized to receive micropipette 20, may be positioned in hole 38 to securely hold the micropipette on adaptor 10.

As best seen in FIG. 4, the base member 24, together with its adjacent resilient members 26, 28 and the holders 30, 32 are all positioned with their respective openings aligned to create a pathway 44 through adaptor 10 along which light can shine. FIG. 4 also shows that a lens 46 is positioned in pathway 44. Specifically, lens 46 is attached or mounted on holder 30 by any means well known in the pertinent art, such as by gluing or solvent bonding. Further, lens 46 may be mounted on holder 30 by a frictional snap-in configuration or held thereon by set screws (not shown). Similarly, a lens 48 is attached or mounted on holder 32 and is positioned in the pathway 44 substantially as shown. For purposes of the present invention, it is preferable that the lenses 46, 48 be cylindrical. This is so in order for the lens 46 (the directing lens) to linearly focus input light beam 18 onto a line which can be positioned along the longitudinal axis of micropipette 20. Further, a cylindrical shape for lens 48 (the receiving lens) is also preferable in order for the linearly focused input light beam 18 to be recollimated as output light beam 22. Preferably, both cylindrical lens 46 and cylindrical lens 48 are made of a quartz material which permits use of either visible or ultraviolet light.

As will be appreciated by the skilled artisan, input light beam 18 can be precisely focused along the longitudinal axis of micropipette 20 by appropriately moving lens 46 in a direction along the pathway 44. In order to linearly focus input light beam 18 and obtain the highest intensity $I(\lambda)$ for the light which is incident on the sample material being held in micropipette 20, the holder 30 on which lens 46 is mounted, can be moved relative to the base member 24 on which micropipette 20 is mounted. As seen in FIG. 4, when lens 46 is properly positioned, input beam 18 will be focused into a line which is coincident with the center of lumen 50 of micropipette 20. Following well known optical principles, light will emerge from micropipette 20 in a predictable fashion. Consequently, cylindrical lens 48 (the receiving lens) can receive this emerging light and recollimate the light into the output light beam 22. To accomplish this, lens 48 is mounted on holder 32 and is movable therewith relative to base member 24. As will be readily appreciated, the resilient members 26, 28 permit selective relative movement between base member 24 and the respective holders 30, 32. At the same time, resilient members 26, 28 provide a support for maintaining the relative positions of these components when they are not being moved. It is possible, however, to completely eliminate the resilient members 26, 28. Manufacturing tolerances may suffice to properly position lens 46 on holder 30 without any further adjustment necessary to predictably focus light from the lens 46 along the interior lumen of micropipette 20. Similarly, lens 48 may be mounted on holder 32 and positioned relative to base member 24 without the need for subsequent adjustments.

The mechanism for moving holders 30, 32 relative to base member 24 will be best seen by referring to FIG. 2 wherein a screw 52 is shown extending through holder 30 and resilient member 26 for threadable connection with base member 24. The screws 54 and 56 likewise connect holder 30 with base member 24. Similarly, screws (of which the screw 58 shown in phantom is exemplary) connect holder 32 with base member 24. In each case, the screws 52, 54, 56, 58 (and others not shown) can be individually rotated to independently move the holders 30, 32 relative to the base member 24. Consequently, this moves lenses 46, 48 relative to micropipette 20.

As intended for the present invention, movement of cylindrical lens 46 relative to micropipette 20 is accomplished to linearly focus input light beam 18 along the axis of micropipette 20. This increases the intensity $I(\lambda)$ of the light which is incident on the sample material held in solution in lumen 50 of micropipette 20. Similarly, movement of the cylindrical lens 48 relative to micropipette 20 is accomplished in order to recollimate the light which emerges from micropipette 20 for easier analysis of its intensity $I_f(\lambda)$ by the detector 16.

Referring now to the embodiment of a micropipette adaptor as shown in FIGS. 5-9, there is shown an adaptor with temperature control which is generally designated 100. The adaptor 100 can generally be thought of as being used in place of adaptor 10 earlier described. In particular, adaptor 100 comprises a base member 110 sandwiched between a layer 112 and a layer 114. Base member 110 is made of a metal material which has high thermal conductivity and is easy to machine, such as copper, brass or aluminum. Layers 112, 114 are made of a different material, preferably nonmetal, such as delrin plastic, which are attached, such as by bonding, to each side of base member 110. The overall dimensions of the adaptor are such that it easily fits into a conventional sample holder slot of a commercially available spectrophotometer. In the embodiment shown, the dimensions of layers 112 and 114 are approximately 12.5 millimeters in width, and approximately 38 millimeters in height. Base member 110 is slightly smaller in these dimensions, i.e. width and height, to prevent heat loss by contact of the base member 110 with the spectrophotometer. Lenses 116 and 118 are mounted in layers 112, 114 respectively, similar to mounting of lenses 46, 48 as earlier shown in FIG. 4.

Base member 110 has an orifice 120 in the top thereof. Orifice 120 is generally cylindrical and vertically oriented in base member 110 for receiving a micropipette containing sample material. Orifice 120 has a top 122 and walls 124 adapted to the shape of the micropipette. Base member 110 has a passageway 126, into which orifice 120 opens at orifice bottom 128. A micropipette which is inserted into orifice 120 then may extend through orifice 120 down into passageway 126. Then a collimated light beam, such as light beam 18 of FIG. 4, can be passed through the sample. Base member 110 further includes a thermocouple 130 for measuring the temperature of base member 110. Thermocouple 130 is preferably a chromel-alumel thermocouple having wires 132, 134, which provide a temperature signal.

Quartz lenses 118, 116 may be held in place with teflon tipped set screws inserted into set screw slots 136. A heater wire 138 is positioned and held between layer 112 and base member 10. It is routed around the perimeter of passageway 126 and is positioned against base member 110 being held firmly in place by layer 112. Heater wire 138 is preferably made of manganin, five thousandths 0.005) inches in diameter. It will be appreciated, however, that tungsten or other resistive type wires are also appropriate for use as heater wire 138. Wire 138 is connected to a direct current power supply (not shown) for heating the wire, with typical values for the output of the supply being from five tenths to one (0.5–1.0) amperes at two to four (2–4) volts.

Thus, the adaptor 100 serves at least two functions, namely maintaining the alignment between the sample and the focusing lenses, and further acting as a thermal reservoir. By applying the proper amount of voltage and power levels to heater wire 138, the base member 110 can be heated. This results in heating of the sample which is contained in a micropipette inserted in orifice 120 to the desired temperature. It has been found, for example, that use of four (4) watts of power may be used to obtain temperatures of a micropipette sample of eighty to one hundred degrees (80°–100°).

Figure 9:
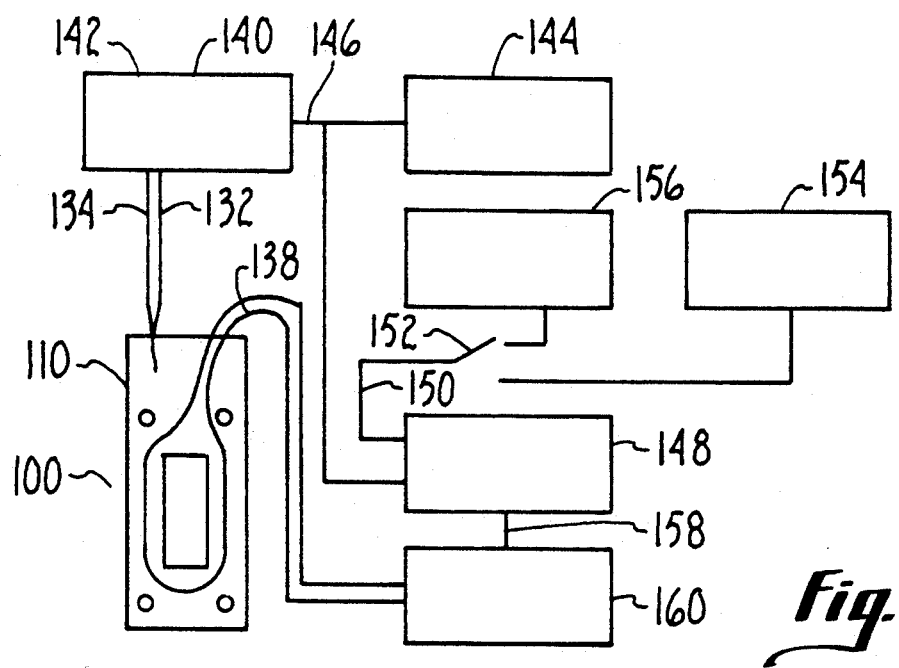
FIG. 9 is a schematic diagram of a feedback control system used in conjunction with the adaptor of FIG. 5 in accordance with the present invention.

There is further shown in FIG. 9 a feedback control system generally indicated as 140 for operably controlling the temperature of adaptor 100. In particular, system 140 comprises a thermocouple circuit 142 connected to thermocouple outputs 132, 134 from base member 110. The temperature output of thermocouple circuit 142 may be displayed by digital panel meter 144. In addition, output 146 of thermocouple circuit 142 is connected to a comparator 148. Also connected as an input to comparator 148 is a set point input signal line 150. The actual measured thermocouple output signal 146 is compared to the set point 150 at comparator 148. Set point signal information 150 can be alternately provided via switch 152 between a signal generated by a temperature set point potentiometer 154, or a signal generated by an analog temperature programming input device 156. Potentiometer 154 can be set by selecting a desired voltage which corresponds to the desired temperature at which the base member is to be maintained. On the other hand, the temperature programming input 156 provides an external input to provide a varying time/temperature wave form using an analog signal. Thus, the set point signal 150 can be programmed to maintain a constant temperature based on the potentiometer 154 setting, or specific temperatures for predetermined periods of time based on the programming input 156. Based upon the comparison between the set point signal 150 and the actual measured temperature signal 146, the comparator generates an "on" or "off" signal 158. This activates or deactivates a transistor heater driver 160. Driver 160 sends a current through heater wire 138 to heat up base member 110 when it is activated, or cuts off the current to allow base member 110 to cool down when it is deactivated.

In one experiment utilizing adaptor 100, the absorption of light at 260 nanometers of DNA was observed and measured as it was being denatured at a temperature of between seventy and eighty degrees centigrade (70°–80° C.). Since double-stranded DNA denatures at these temperatures, it was found that the absorption at 260 nanometers increased by approximately thirty-seven percent (37%). The melting temperature, or denaturing temperature, is approximately eighty-three degrees (83°). Thus, by ramping the temperature rapidly by applying one ampere to the adaptor 100, the temperature was allowed to ramp upward after reaching seventy degrees centigrade (70° C.), which is the temperature at which DNA should begin to denature. Using the adaptor 100 of the present invention took approximately ten minutes to reach eighty degrees centigrade (80° C.) from twenty-three degrees centigrade (23° C.). The absorbance of the sample used, namely Lambda DNA markers, at a concentration of 675 micrograms per milliter, changed from 0.589 before denaturing to 0.737 after denaturing, or changed approximately twenty-five invention can readily be appreciated by those skilled in the art.

Figure 10:
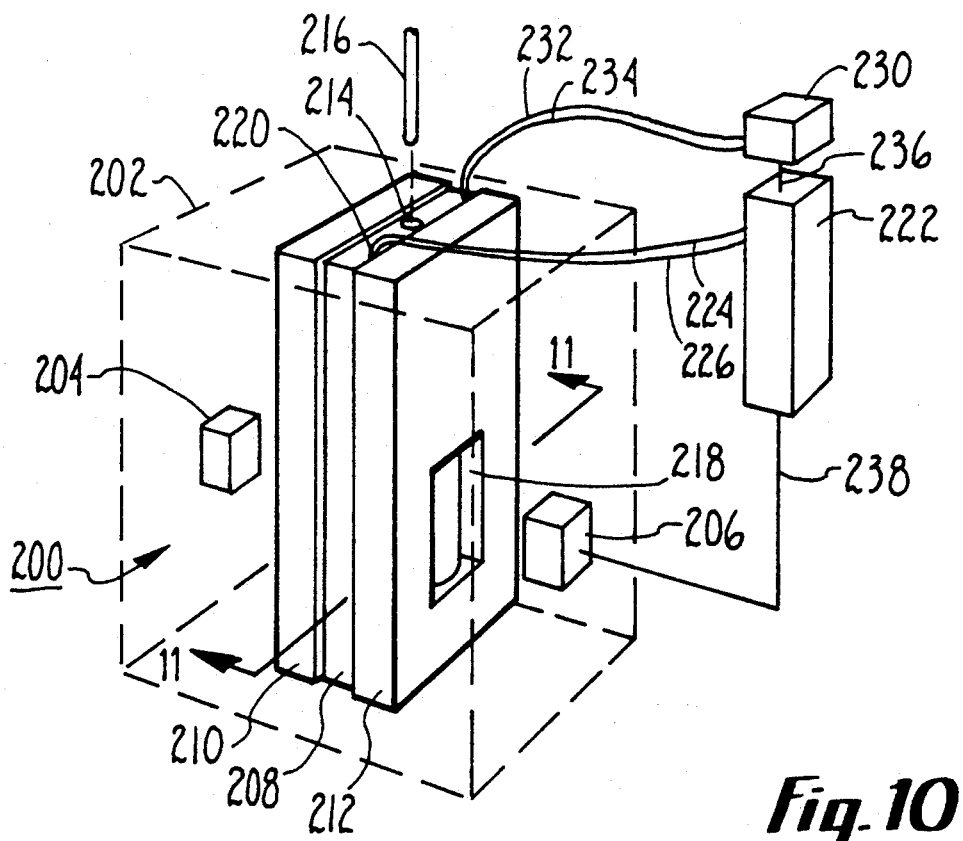
FIG. 10 is a perspective view of an alternate embodiment of the micropipette adaptor with a spectrometric feedback control system, with portions shown in phantom for clarity.
Figure 11:
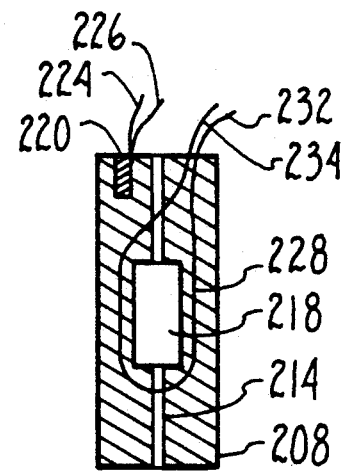
FIG. 11 is a cross-sectional view of the adaptor, as seen along the line 11—11 in FIG. 10.

FIG. 10 shows a system which includes a micropipette adaptor, generally designated 200, in operative association with a spectrometer 202 (shown in phantom) for monitoring and controlling the cyclic heating of a sample solution. Spectrometer 202 includes a light source 204 and a light receiver 206. It is to be understood that micropipette adaptor 200 is in all essential respects identical to micropipette adaptor 100. More particularly, micropipette adaptor 200 has a metallic base member 208 sandwiched between non-metallic layers 210, 212. Base member 208 is formed with an orifice 214 that is dimensioned for receiving a micropipette 216. Micropipette 216 contains the sample solution to be analyzed. A passageway 218 is formed through layers 210, 212 and base member 208 such that a path for light is established through passageway 218 from source 204 to receiver 206 when adaptor 200 is properly positioned in spectrometer 202. Base member 208 also has a temperature-sensitive thermocouple 220 disposed in member 208. Thermocouple 220 is electrically connected to a microprocessor 222 through wires 224, 226. Finally, in cross-reference to FIGS. 10 and 11, a manganin heater wire 228 is electrically connected to a voltage source 230 through wires 232, 234. Voltage source 230 is any appropriate voltage source which can cause heater wire 228 to become hotter when voltage source 230 electrically energizes heater wire 228. Voltage source 230 is in turn electrically connected to microprocessor 222 through electrical wire 236. Finally, FIG. 1 shows that microprocessor 222 is electrically connected through wire 238 to light receiver 206.

It is to be appreciated that the system disclosed above is useful for monitoring and optimizing the cyclic heating of the sample solution which can be held in micropipette 216. As an example of one cyclic heating process which can be monitored and controlled by the system shown in FIG. 10, the solution held in micropipette 216 may contain a particular type of DNA molecule which is to be amplified by a PCR amplification technique. Accordingly, microprocessor 222 will have stored in its memory a predetermined time-dependent temperature profile which is to be imposed on the DNA solution within micropipette 216 to accomplish PCR amplification. To impose the predetermined temperature profile on the solution held within micropipette 216, microprocessor 222 monitors the temperature signal of thermocouple 220, which is transmitted to microprocessor 222 through wires 224, 226. In response to the temperature signal from thermocouple 220, microprocessor 222 selectively energizes voltage source 230 (and, hence, heater wire 228) to thereby establish a time-dependent temperature of the solution held within micropipette 216 in accordance with the predetermined temperature profile.

Figure 12:
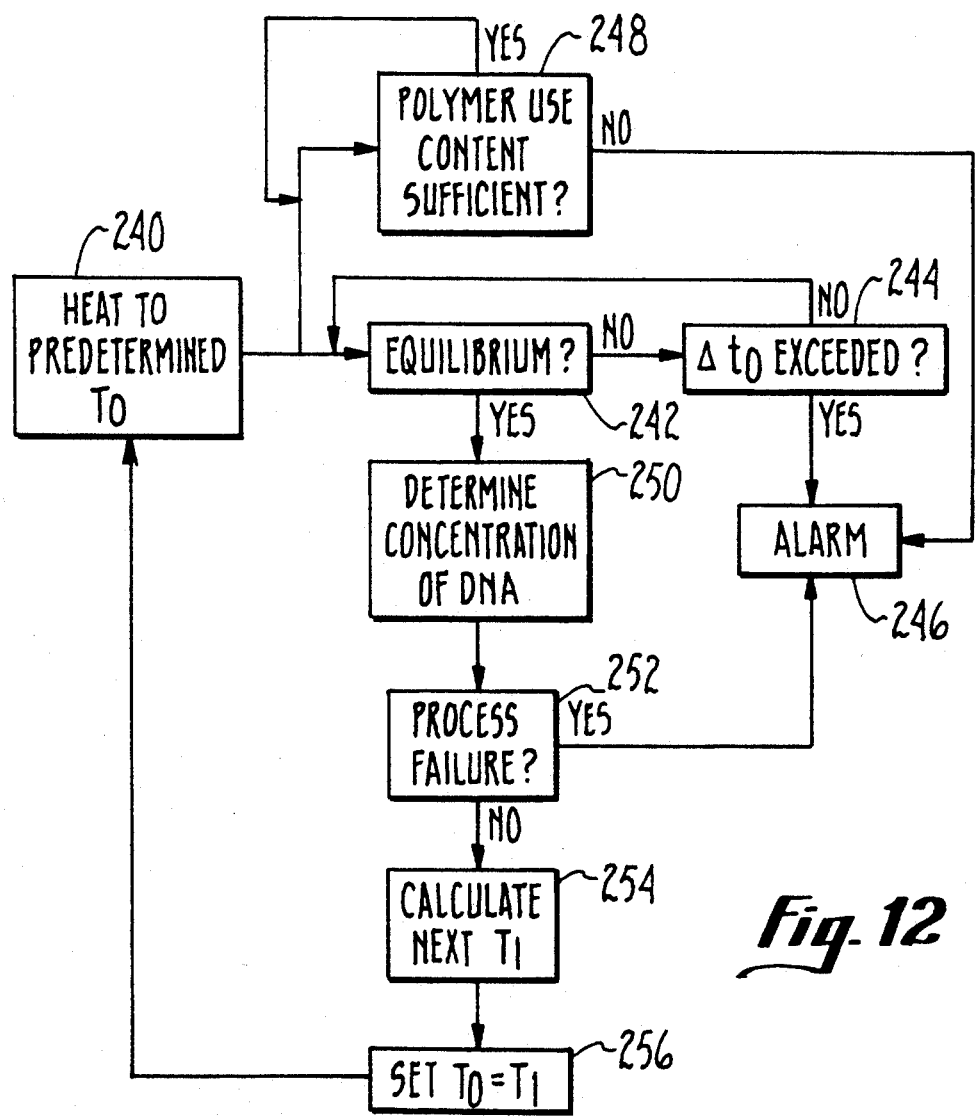
FIG. 12 is a logic flow chart of the microprocessor of the system shown in FIG. 10.

Importantly, the predetermined temperature profile can be altered in response to the output signal from light receiver 206, to optimize the particular cyclical heating technique, e.g. PCR amplification of DNA. FIG. 12 shows the logic used by microprocessor 222 to monitor a single heating step in the predetermined temperature profile and to alter the predetermined temperature profile.

As indicated at block 240, microprocessor 222 selectively energizes voltage source 230 (and, hence, heater wire 228) to heat the solution held within micropipette 216 to a predetermined temperature $T_0$. Then, as indicated at block 242, microprocessor 222 monitors the electromagnetic interaction characteristics of the solution held within micropipette 216, as indicated by light receiver 206. More particularly, for the specific but non-limiting example wherein a PCR amplification technique is used to amplify DNA held in solution in micropipette 216, the light absorption characteristics at 280 nm and 260 nm of the solution held within micropipette 216 are monitored by microprocessor 222. As is well known to the skilled artisan, the light absorption characteristics at 260 nm of the solution held in micropipette 216 are representative of the total amount of double stranded, single stranded and nucleotide DNA components within micropipette 216. Consequently, as the amount of DNA components in solution changes during the PCR amplification process, the light change. Accordingly, by monitoring the light absorption characteristics at 260 nm of the solution within micropipette 216, microprocessor 222 can determine, in accordance with well known principles, when the DNA in solution has reached equilibrium during the monitored heating step.

When microprocessor 222 determines that DNA equilibrium has not been reached, the logic of microprocessor 222 proceeds to block 244. Otherwise, the logic of microprocessor 222 proceeds to block 250. More specifically, DNA equilibrium may not be reached within an acceptable predetermined time period $\Delta t_o$, in which case a PCR amplification process error may be indicated. Accordingly, in the event that the DNA in solution does not reach equilibrium within the predetermined time period $\Delta t_o$ as indicated at block 244, an alarm can be activated as indicated at block 246. Otherwise, the logic of microprocessor 222 returns to block 242.

As indicated at block 248, microprocessor 222 also monitors the polymerase protein content of the solution by monitoring the light absorption characteristics of the solution in micropipette 216 at 280 nm, in parallel with the DNA monitoring described above. As is well known in the art, the polymerase protein which is a necessary constituent in the PCR amplification process absorbs light that has a wavelength of 280 nm. Accordingly, the polymerase content of the solution in micropipette 216 can be monitored by microprocessor 222 as indicated at block 248 by monitoring the light absorption characteristics of the solution in micropipette 216 at 280 nm. When the polymerase concentration of the solution in micropipette 216 falls below a predetermined level, an alarm can be sounded, as indicated at block 246. Such an alarm would accordingly indicate that there is insufficient polymerase protein in solution to support effective PCR amplification.

Still referring to FIG. 12, once equilibrium of the DNA in solution in micropipette 216 has successfully been reached, microprocessor 222 calculates the concentration of DNA in solution by well-known methods of spectroscopy. This step is represented by block 250. The concentration of DNA calculated at block 250 is compared to a predetermined concentration value at block 252 to determine whether a PCR amplification process error has occurred. More specifically if a PCR amplification process has occurred, the concentration of DNA in solution will be less than the predetermined, "expected" concentration of DNA. This predetermined concentration can be the DNA concentration value from the immediately preceding step or cycle, or some other empirically desired value. If microprocessor 232 determines that a process error has occurred at block 252, an alarm is activated as indicated at block 246. Otherwise, microprocessor 222 calculates a temperature $T_1$, as indicated at block 254, at which the solution in micropipette 216 is to be held during the subsequent cycle or step in the PCR amplification process. To this end, $T_0$ is set equal to $T_1$, as indicated at block 256. Importantly, the value of $T_1$ can depend on the concentration of DNA in solution, as calculated by microprocessor 222 at block 250, as well as the length of time it took the DNA in solution to reach equilibrium, as determined at block 242 by microprocessor 222. The logic of microprocessor 222 then returns to block 240 and repeats the process indicated above for succeeding steps of the PCR amplification process.

It is to be understood that while the discussion above focussed on a method for monitoring a PCR amplification process, the present invention may be used in a wide variety of other applications. Indeed, the present invention is useful for monitoring and controlling any process in which a solution whose light interaction characteristics change with temperature is cyclically heated and cooled within a micropipette.

While the particular micropipette adaptor for spectrophotometers with temperature control as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A system for monitoring the heating of a solution having temperature-dependent light absorption characteristics in a spectrometer having a light source and a light receiver for generating an output signal, which comprises:

a substantially transparent container for holding said solution;

a base formed with a cavity therethrough for receiving said container, said base being positionable within said spectrometer to establish a pathway for light from said light source of said spectrometer through said cavity and said container to said light receiver of said spectrometer;

a heating element mounted in said base adjacent said cavity for heating said container; and a microprocessor electrically connected to said light receiver and said heating element for selectively energizing said heating element in response to said output signal of said light receiver.

2. A system as recited in claim 1 further comprising a voltage source electrically connected to said heating element and said microprocessor.

3. A system as recited in claim 2 wherein said heating element is a coated manganin wire and said base is metal.

4. A system as recited in claim 3 wherein said wire circumscribes said cavity.

5. A method for controlling the heating of a solution within a spectrometer, which comprises the steps of:

holding said solution in a transparent container;

holding said container in a base having a cavity formed therethrough for receiving said container, said base having a heating element mounted therein in juxtaposition with said cavity;

orienting said base and said container in said spectrometer to establish a path for light transmission from the light source of said spectrometer, through said cavity and said container, to the light receiver of said spectrometer; and selectively energizing said heating element in response to the output signal of said light receiver to selectively heat said solution.

6. An apparatus for controlling the heating of a solution in a spectrometer having a light source and a light receiver having an output signal, which comprises:

a heating element;

means for holding said heating element in juxtaposition with said solution, said holding means further comprising container means for holding said solution between said light source and said light receiver; and control means electrically connected to said heating element and said light receiver for selectively energizing said heating element in response to said output signal of said light receiver.

7. An apparatus as recited in claim 6 further comprising energizing means electrically connected to said heating element and said control means for energizing said heating element.

8. An apparatus as recited in claim 7 wherein said energizing means is a voltage source.

9. An apparatus as recited in claim 8 wherein said container means is a transparent container.

10. An apparatus as recited in claim 9 wherein said holding means is a base formed with a cavity therethrough for receiving said container, said base being positionable in said spectrometer to establish a pathway for light from said light source, through said cavity and said container, and to said light receiver.

11. An apparatus as recited in claim 10 wherein said control means is a microprocessor, said microprocessor being electrically connected to said voltage source for selectively energizing said voltage source to energize said heating element for a predetermined time.

12. An apparatus as recited in claim 11 wherein said heating element is a coated manganin wire and said base is metal.

13. An apparatus as recited in claim 12 wherein said wire circumscribes said cavity.

14. An apparatus as recited in claim 11 wherein said heating element is a thermoelectric heater/cooler.

* * * * *